(12) United States Patent
Giannotti et al.

(10) Patent No.: US 9,550,743 B2
(45) Date of Patent: Jan. 24, 2017

(54) PROCESS FOR THE PREPARATION OF AN ANTIDEPRESSANT AND THE INTERMEDIATES THEREOF

(71) Applicant: DIPHARMA FRANCIS s.r.l., Baranzate (IT)

(72) Inventors: Luca Giannotti, Baranzate (IT); Renzo Graziosi, Baranzate (IT); Emanuele Attolino, Baranzate (IT); Pietro Allegrini, Baranzate (IT)

(73) Assignee: Dipharma Francis S.r.l., Baranzate (IT)

( * ) Notice: Subject to any disclaimer, the term of this patent is extended or adjusted under 35 U.S.C. 154(b) by 0 days.

(21) Appl. No.: 14/945,654

(22) Filed: Nov. 19, 2015

(65) Prior Publication Data
US 2016/0145224 A1    May 26, 2016

(30) Foreign Application Priority Data
Nov. 21, 2014 (IT) .............................. MI2014A2018

(51) Int. Cl.
*C07D 295/096* (2006.01)
*C07C 323/37* (2006.01)
*C07C 309/66* (2006.01)
*C07D 241/08* (2006.01)

(52) U.S. Cl.
CPC ......... *C07D 295/096* (2013.01); *C07C 309/66* (2013.01); *C07C 323/37* (2013.01); *C07D 241/08* (2013.01)

(58) Field of Classification Search
CPC .................................................. C07D 295/096
See application file for complete search history.

(56) References Cited

FOREIGN PATENT DOCUMENTS

| WO | 03029232 A1 | 4/2003 |
|---|---|---|
| WO | 2007144005 A1 | 12/2007 |
| WO | 2013102573 A1 | 7/2013 |
| WO | 2014161976 A1 | 10/2014 |
| WO | 2014191548 A1 | 12/2014 |

OTHER PUBLICATIONS

Benny Bang-Andersen et al: "Discovery of 1-[2-(2,4 Dimethylphenylsulfanyl)phenyl]piperazine (Lu AA21004): A Novel Multimodal Compound for the Treatment of Major Depressive Disorder", Journal of Medicinal Chemistry, vol. 54, No. 9, May 12, 2011 (May 12, 2011), pp. 3206-3221, XP055058222, ISSN: 0022-2623, DOI: 10.1021/jm101459g.

Uldam H K et al: "Biosynthesis and identification of an N-oxide/N glucuronide metabolite and first synthesis of an N—O-Glucuronide metabolite of Lu AA21004", Drug Metabolism and Disposition, Pharmacology and Experimental Therapeutics, US, vol. 39, No. 12, Sep. 6, 2011 (Sep. 6, 2011), pp. 2264-2274, XP002714028, ISSN: 0090-9556, DOI: 10.1124/DM D.111.040428, [retrieved on Sep. 6, 2011].

Search Report cited in the corresponding Italian Application No. MI20142018 dated Jan. 29, 2015, 11 pages.

*Primary Examiner* — Bruck Kifle
(74) *Attorney, Agent, or Firm* — Rothwell, Figg, Ernst & Manbeck, P.C.

(57) ABSTRACT

The present invention relates to a process for the preparation of 1-[2-(2,4-dimethylphenylsulphanyl)phenyl]piperazine of formula (I), also known as vortioxetine, salts thereof, and intermediates useful for its synthesis.

19 Claims, No Drawings

PROCESS FOR THE PREPARATION OF AN ANTIDEPRESSANT AND THE INTERMEDIATES THEREOF

FIELD OF INVENTION

The present invention relates to a process for the preparation of 1-[2-(2,4-dimethylphenylsulphanyl)phenyl]piperazine of formula (I), also known as vortioxetine, salts thereof, in particular the hydrobromide, and intermediates useful for the synthesis thereof.

PRIOR ART

Vortioxetine, namely 1-[2-(2,4-dimethylphenylsulphanyl)phenyl]piperazine, of formula (I), is an atypical antidepressant that performs a combined SERT-inhibitor, 5-$HT_3$ antagonist and partial 5-$HT_{1A}$ agonist action.

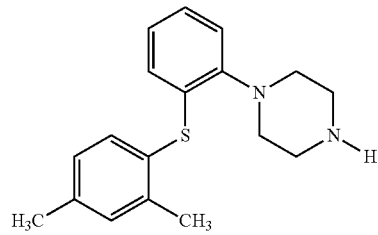

(I)

Vortioxetine is present on the market as the hydrobromide salt, under the tradename Brintellix®.

Vortioxetine is known from WO 03/029232 (Example 1e). US 2014/0163043 discloses the synthesis of vortioxetine by alkylation of the aniline of formula (II) with the chloride of formula (A) or the bromide of formula (B), as follows:

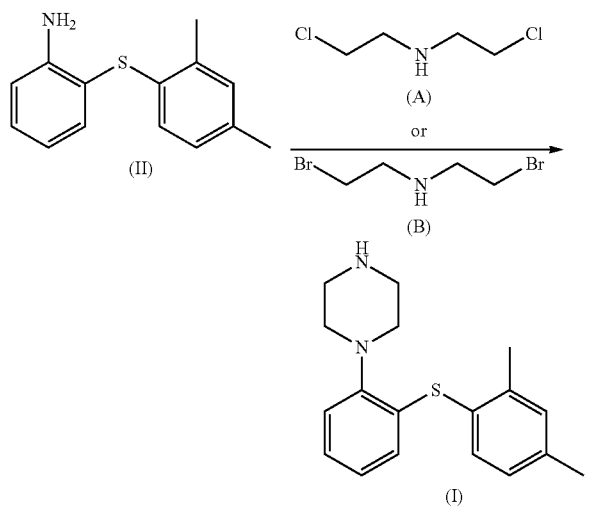

However, said synthesis was not exemplified in the experimental part.

The authors of the present invention attempted in any event to convert the aniline of formula (II) to vortioxetine under different reaction conditions, using the compound of formula (A) or the hydrochloride salt thereof as alkylating agent, and did obtain vortioxetine but with low yields, always below 35%. In an attempt to improve the reaction yields, the amino group of a compound of formula (A) was protected by the authors of the invention both as tert-butyloxycarbonyl (Boc) and as acetamide, but in both cases the alkylation reaction of a compound of formula (II) entirely failed to work.

WO 2007/144005 discloses the synthesis of vortioxetine with a good yield and in a single synthesis step, by reacting the aryl halide of formula (C) with the 2,4-dimethylthiophenol of formula (D) and the piperazine of formula (E) in the presence of a palladium-based catalyst, a phosphine ligand and a base.

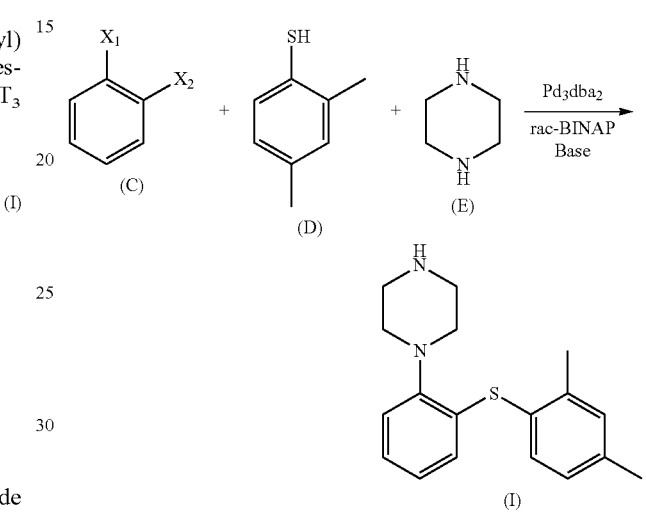

Despite the good performance of this process in terms of both yield and productivity, the synthesis is very expensive due to the presence of the Pd catalyst, and especially of the complex phosphines used as ligands.

There is consequently a need for an alternative, improved vortioxetine preparation method which is simpler, more advantageous and cheaper. Said method should in particular involve the use of more efficient, cheaper, simpler reaction conditions so as to obtain vortioxetine advantageously, with a higher yield and better process economy.

SUMMARY OF THE INVENTION

The invention provides a process for the preparation of a compound of formula (III) or a salt thereof,

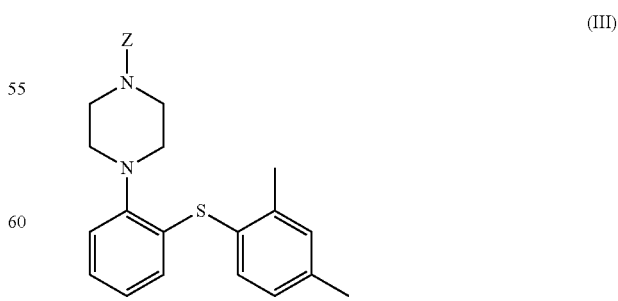

(III)

wherein Z is as defined herein, comprising the formation of the piperazine ring, using as intermediate a compound of formula (IV)

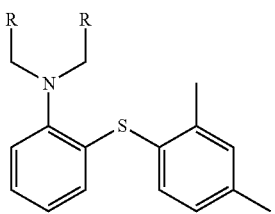

(IV)

as defined herein. Vortioxetine is the compound of formula (III), wherein Z is hydrogen.

DETAILED DESCRIPTION OF THE INVENTION

The subject of the invention is a process for the preparation of a compound of formula (III), or a salt thereof,

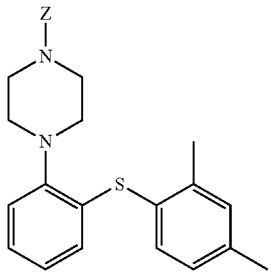

(III)

wherein Z is H or an amino protecting group, comprising the reaction between a compound of formula (IV), or a salt thereof,

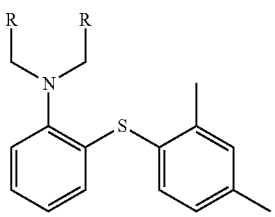

(IV)

wherein each of the R substituents is an aldehyde group —CHO, or each of the R substituents, being the same or different, is a carboxyl group COOH or a reactive derivative thereof, or each of the R substituents, which are equal or different, is a CH$_2$X group, wherein X is an halogen atom or a good leaving group, with a compound of formula (V), or a salt thereof,

(V)

wherein Z is as defined above, and, if applicable, conversion of a compound of formula (III) to another compound of formula (III) or a salt thereof, and/or conversion of a salt of a compound of formula (III) to its free base.

A salt of a compound of formula (III), (IV) or (V) is typically a pharmaceutically acceptable salt thereof. In particular a salt of a compound of formula (III), (IV) or (V) is the hydrobromide or the hydrochloride.

Z as amino protecting group is, for example, a protecting group known from peptide chemistry, such as benzyl, benzyloxycarbonyl and tert-butyloxycarbonyl, preferably benzyl.

A reactive derivative of carboxyl group —COOH is, for example, a —COW group, wherein W is an OR$_1$ group, wherein R$_1$ is a C$_1$-C$_6$ alkyl, aryl or heteroaryl group, wherein said group is optionally substituted; or W is an halogen atom, preferably chlorine.

X in a —CH$_2$X group as an halogen atom is preferably chlorine or bromine, or as a good leaving group is typically an R$_2$SO$_3$— group, wherein R$_2$ is a C$_1$-C$_6$ alkyl or an aryl group, wherein said group is optionally substituted.

In a —CH$_2$X group, X is preferably a chlorine or bromine atom, or mesylate or tosylate.

A C$_1$-C$_6$ alkyl group, which can be straight or branched, is typically a C$_1$-C$_4$ alkyl group, such as methyl, ethyl, propyl, isopropyl, butyl, isobutyl or tert-butyl, which can be substituted by one or more substituents that may be the same or different, preferably by one to three substituents, such as halogen, for example chlorine or fluorine.

An aryl or heteroaryl group can be, for example, a phenyl or 1-imidazolyl group respectively, typically phenyl.

Said aryl group can be optionally substituted by one to three substituents selected independently from a straight or branched C$_1$-C$_4$ alkyl group, which in its turn can optionally be substituted by one to three halogen atoms, typically fluorine; a hydroxy group; a C$_1$-C$_4$ alkoxy group, such as methoxy; a halogen atom, such as bromine or chlorine; a cyano group; and a nitro group.

In a compound of formula (IV), or a salt thereof, the two R substituents are preferably equal.

The reaction between a compound of formula (IV), as defined above, wherein each of R is an aldehyde group —CHO, and a compound of formula (V), as defined above, can be performed under the conditions specified for the reductive amination reaction, in the presence of a reducing agent and a solvent.

In a compound of formula (V), Z is preferably H or benzyl.

A reducing agent can be, for example, NaCNBH$_3$ or NaB(OAc)$_3$H, optionally generated in situ from NaBH$_4$ and acetic acid, or a homogenous or heterogeneous palladium (Pd) or platinum (Pt) metal based catalyst and molecular hydrogen, or a homogenous or heterogeneous palladium (Pd) or platinum (Pt) metal based catalyst and a suitable hydrogen donor under hydrogen transfer conditions, as known in the art.

A solvent can be an organic solvent selected, for example, from the group comprising a polar aprotic solvent, typically dimethylformamide, dimethylacetamide, acetonitrile or dimethylsulphoxide; a cyclic or acyclic ether, typically tetrahydrofuran, dioxane or methyl-tertbutyl ether; a chlorinated solvent, typically dichloromethane; an apolar aprotic solvent, typically toluene or hexane; a polar protic solvent, such as a straight or branched C$_1$-C$_6$ alkanol, in particular methanol, ethanol, isopropanol, n-butanol, tert-butanol or water; an ester, such as ethyl acetate, isopropyl acetate or butyl acetate; or a mixture of two or more, preferably two or three, of said solvents.

The reaction between a compound of formula (IV), as defined above, wherein each of R, being the same or different, is a —COOH group or a reactive derivative thereof, and a compound of formula (V), as defined above, can be performed under known amidation conditions between a carboxylic acid or a reactive derivative thereof, typically an ester or acid chloride thereof, with an amine, forms of an intermediate of formula (VI)

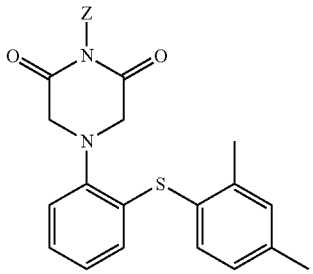

(VI)

wherein Z is as defined above, which can be converted to a compound of formula (III) by subsequent reduction with a hydride, such as NaBH$_4$ or LiAlH$_4$, in a solvent. In this case, depending on the conditions used, for instance the amount of reducing agent, the reduction reaction can include the formation of an intermediate of formula (VII), or a salt thereof,

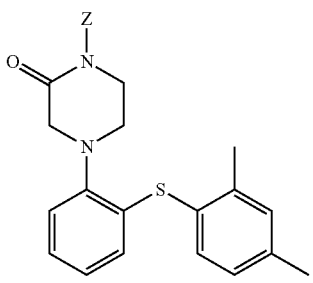

(VII)

wherein Z is as defined above.

In a compound of formula (V), Z is preferably H or benzyl.

The reaction between a compound of formula (IV), wherein each of R, being the same or different, is a —CH$_2$X group, as defined above, and a compound of formula (V), can be performed under the conventional conditions for alkylation reactions, optionally in the presence of a base and a solvent.

Said alkylation reaction can be performed at a temperature ranging between about 0° C. and the solvent reflux temperature, preferably between about 10° C. and about 60° C.

A base, which can be an organic or inorganic base, is in particular, an inorganic base, preferably an alkali metal hydroxide or alkaline earth metal hydroxide, a phosphate, a carbonate or a bicarbonate, or an organic base, preferably a tertiary amine, such as triethylamine, diisopropylethylamine or N-methyl morpholine.

The reaction between a compound of formula (IV), wherein R is a —COOH group or a reactive derivative thereof, or R is a —CH$_2$X group, as defined above, and a compound of formula (V), as defined above, can be performed in an organic solvent selected, for example, from the group comprising a polar aprotic solvent, typically dimethylformamide, dimethylacetamide, acetonitrile and dimethylsulphoxide; a cyclic or acyclic ether, typically tetrahydrofuran, dioxane or methyl-tertbutyl ether; a chlorinated solvent, typically dichloromethane; an apolar aprotic solvent, typically toluene or hexane; a polar protic solvent, such as a straight or branched C$_1$-C$_6$ alkanol, in particular methanol, ethanol, isopropanol, n-butanol, tert-butanol or water; an ester, such as ethyl acetate, isopropyl acetate or butyl acetate; a straight or branched C$_3$-C$_7$ ketone, such as acetone, methylethyl ketone or methyl isobutyl ketone; or a mixture of two or more, preferably two or three, of said solvents.

The alkylation reaction is preferably performed with a compound of formula (V) wherein Z is H or benzyl.

According to a particularly preferred aspect of the invention, the alkylation reaction can be performed with a compound of formula (V), wherein Z is H, and consequently the compound of formula (V) is ammonia, which is used in excess without the presence of an additional base.

The skilled person will realise that in the reactions illustrated above, when in a compound of formula (V) Z is H, in the resulting compound of formula (III) Z is H, namely vortioxetine of formula (I).

A compound of formula (III), thus obtained, if convenient, can be converted into another compound of formula (III) or a salt thereof, typically the hydrobromide; or a salt of a compound of formula (III) can be converted into its free base, by known methods.

For example, a compound of formula (III), wherein Z is an amino protecting group, can be converted to another compound of formula (III) wherein Z is H, namely the vortioxetine of formula (I), by known methods, for example by the deprotection methods known from peptide chemistry.

Similarly, the conversion of a compound of formula (III), wherein Z is H, to another compound of formula (III), wherein Z is an amino protecting group, can be performed by methods known to the skilled person.

Analogously a compound of formula (III) can be converted into a salt thereof, typically the hydrobromide; or a salt of a compound of formula (III) can be converted into its free base, by methods known in the art.

A further subject of the invention is a process for the preparation of vortioxetine of formula (I) or a salt thereof, in particular the hydrobromide, comprising the use as intermediate of a compound of formula (IV) or a salt thereof as defined above.

A compound of formula (IV) or a salt thereof, as defined above, can be obtained, for example, from a compound of formula (VIII)

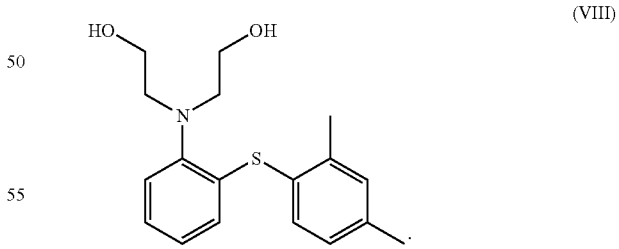

(VIII)

For example, a compound of formula (IV), wherein each of R is an aldehyde group —CHO, can be obtained by oxidation of the hydroxyl functions of a compound of formula (VIII) by known oxidation reactions, typically by Swern oxidation, and in general of activated DMSO (dimethyl sulfoxide), or by oxidation catalysed by TEMPO or by metal derivatives with a high oxidation state, such as tetrapropylammonium perruthenate (TPAP) or pyridinium chlorochromate (PCC).

A compound of formula (IV), wherein each of R, being equal, is a carboxyl group —COOH, or a reactive derivative thereof, can be obtained, for example, from a compound of formula (VIII), as defined above, or from a compound of formula (IV) wherein each of R is —CHO, by oxidation of the respective hydroxyl or aldehyde functions, and optional conversion of the resulting carboxyl function to a reactive derivative such as acid chloride or ester, under known conditions.

A compound of formula (IV) wherein each of R, being equal, is a —CH$_2$X group, wherein X is a halogen atom, can be obtained by substitution of the hydroxyl functions of a compound of formula (VIII) with halogen atoms, for example by treating a compound of formula (VIII) with hydrochloric acid in the presence of ZnCl$_2$ or hydrobromic acid, or with halogenating agents such as SOCl$_2$ or PCl$_3$.

A compound of formula (IV) wherein each of R, being equal, is a —CH$_2$X group as defined above, wherein X is a good leaving group such as R$_2$SO$_3$—, can be obtained by activating the hydroxyl functions of a compound of formula (VIII) by treating with a chloride of formula (IX) or an anhydride of formula (X), respectively:

R$_2$SO$_2$Cl (IX)

R$_2$SO$_2$OSO$_2$R$_2$ (X)

wherein R$_2$ is as defined above. A compound of formula (VIII) can preferably be converted to a compound of formula (IV), wherein each of R is CH$_3$SO$_3$—CH$_2$—, by treatment with mesyl chloride, for example in the presence of an organic base and a solvent as defined above.

A compound of formula (IV), as defined above, wherein the R substituents are different from —CHO or two of R substituents, being the same, are different from —COOC$_2$H$_5$, and the salts thereof, typically a pharmaceutically acceptable salt thereof, is a novel compound and represents a further subject of the invention.

A salt of a compound of formula (IV), (VI), (VII) or (VIII) is typically a pharmaceutically acceptable salt and can be obtained by known methods.

The compounds of formula (IV), (VI), (VII) and (VIII), as defined above, or a salt thereof, have proven to be useful as intermediates for the preparation of a compound of formula (III) as defined above, and in particular vortioxetine of formula (I), by the process according to the invention.

Another aspect of the invention is therefore a process for the preparation of a compound of formula (III) as defined above, and in particular vortioxetine of formula (I), that comprises using a compound of formula (IV), (VI), (VII) or (VIII), as defined above, as intermediate.

A compound of formula (IV) wherein each of R is a —CH$_2$X group, wherein X is a halogen atom, can also be obtained from a compound of formula (II),

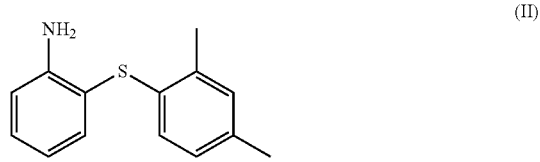 [SMILES: Cc1ccc(Sc2ccccc2N)c(C)c1]

(II)

for example by treatment with 1,2-dichloroethane, 1,2-dibromoethane or 1-bromo-2-dichloroethane, optionally in the presence of a base and a solvent, according to known methods.

A compound of formula (IV) wherein each of R is a —CH$_2$X group, as defined above, wherein X is a good leaving group such as R$_2$SO$_3$—, can also be obtained from a compound of formula (II), for example by treatment with 1,2-methanesulphonyl oxyethane, optionally in the presence of a base and a solvent, by known methods.

A compound of formula (VIII), or a salt thereof, can be prepared from a compound of formula (II) or a salt thereof, for example by alkylation of a compound of formula (II) with 2-bromoethanol, optionally in the presence of a base and a solvent, by known methods.

A compound of formula (II) can be prepared as reported in WO 03/029232 or US 2014/0163043.

It has now surprisingly been found that any crystalline form of vortioxetine hydrobromide can be obtained from vortioxetine base, or a salt thereof, by the process according to the invention, with a chemical purity equal to or greater than 99.5%, in particular equal to or greater than 99.9%, calculated by HPLC (A %).

A further subject of the invention is therefore a process for obtaining vortioxetine or a salt thereof, in particular the hydrobromide, with high chemical purity equal to or greater than 99.5%, preferably equal to or greater than 99.9%, calculated by HPLC (A %), comprising the preparation of vortioxetine or a salt thereof by the process according to the invention.

The following examples further illustrate the invention.

EXAMPLE 1

Synthesis of
2-(2,4-dimethylphenylsulphanyl)-aniline
hydrochloride of Formula (II)

In a 250 ml 4-necked flask fitted with a mechanical stirrer, thermometer and condenser, 2,4-dimethylthiophenol (9.2 g, 0.0667 mol) is dissolved in DMSO (25 ml) at room temperature under nitrogen, and K$_2$CO$_3$ (8.78 g, 0.0636 mol) is added. The reaction mixture is then treated by slow dripping with a solution of 2-chloronitrobenzene (10 g, 0.0636 mol) dissolved in DMSO (15 ml). When the reaction is complete the mixture is heated to 80° C. and a 1M solution of NaOH (60 ml) is dripped into it. The resulting suspension is cooled to 15° C. and the solid formed is filtered, washed with H$_2$O (3×30 ml) and stove-dried under vacuum at 50° C. to a constant weight. 16.2 g of the product are obtained with a yield of 93% calculated by NMR analysis, using a decane as internal standard.

$^1$H-NMR (300 MHz, CDCl$_3$) δ: 8.24 (1H, dd, J=4 J=1.5 Hz), 7.46 (1H, d, J=7.8 Hz), 7.34-7.28 (2H, m), 7.21-7.09 (3H, m), 6.71 (1H, dd, J=8.1 J=1.2 Hz), 2.39 (3H, s), 2.30 (3H, s).

The product previously obtained (37.7 g, 0.144 mol) is then dissolved in THF (226 ml) in a 500 ml 4-necked flask fitted with a mechanical stirrer, thermometer and condenser, under nitrogen. The solution is treated with powdered zinc (37.7 g, 0.580 mol), and the mixture is heated to 50° C. and then treated by slow (about 180 minutes) dripping with acetic acid (49 ml, 0.864 mol), maintaining the temperature between 60 and 65° C. during dripping. When the reaction is complete the mixture is filtered and the solvent distilled at low pressure. The residue obtained is taken up with toluene (250 ml), and the organic phase is washed with a 1M solution of NaOH (2×200 ml) and a saturated solution of NaCl (200 ml).

The organic phase is then heated to 50° C. and treated with HCl to pH=1. The resulting suspension is cooled to 15°

C. and filtered. The solid is washed with toluene (2×60 ml) and stove-dried under vacuum at 50° C. to a constant weight. 32 g of 2-(2,4-dimethylphenylsulphanyl)-aniline hydrochloride of formula (II) is obtained with a yield of 83%, calculated by NMR analysis of the solid and using 1,4-dimethoxybenzene as internal standard.

$^1$H-NMR (300 MHz, DMSO-d6) δ: 7.28-7.21 (2H, m), 7.1-7.06 (2H, m), 6.97-6.88 (3H, m), 2.30 (3H, s), 2.24 (3H, s).

EXAMPLE 2

Synthesis of (bis-2-hydroxyethyl)-(2,4-dimethylphenylsulphanyl)-aniline of Formula (VIII)

In a 500 ml 4-necked flask fitted with a mechanical stirrer, thermometer and condenser, under nitrogen, the compound of formula (II) obtained in Example 1 (3 g; 0.011 mol) is suspended at room temperature in a mixture of toluene (25 ml) and H$_2$O (25 ml). 30% NaOH (2.2 ml, 0.022 mol) is added, and the phases are separated. The aqueous phase is extracted with toluene (25 ml) and the combined organic phases are concentrated at low pressure. Bromoethanol (27.2 ml, 0.384 mol) and K$_2$CO$_3$ (7.9 g, 0.0572 mol) are then added to the residue thus obtained, and the mixture is heated at 70° C. for 16 hours.

The mixture is then cooled to room temperature, diluted with toluene (2×30 ml) and treated with water (30 ml). The phases are separated and the organic phase is washed with a saturated solution of NaHCO$_3$ (30 ml) and a saturated solution of NaCl (30 ml), then dried on Na$_2$SO$_4$, and the solvent is eliminated at low pressure.

The oily residue thus obtained is purified by flash chromatography (toluene:AcOEt:aqueous NH$_3$=6:4:0.01) on silica gel. 2.3 g of (bis-2-hydroxyethyl)-(2,4-dimethylphenylsulphanyl)-aniline of formula (VIII) is obtained as oil, with a yield of 65%.

$^1$H-NMR (300 MHz, CDCl$_3$) δ: 7.42 (1H, d, J=7.8 Hz), 7.26-6.94 (5H, m) 6.46 (1H, d, J=7.8 Hz), 3.61 (4H, t, J=4.2 Hz), 3.22 (4H, t, J=5.4 Hz) 2.37 (3H, s), 2.32 (3H, s).

HPLC-MS (APCI)=318.19 [M+1]

EXAMPLE 3

Synthesis of (bis-2-hydroxyethyl)-(2,4-dimethylphenylsulphanyl)-aniline hydrochloride of Formula (VIII)

In a 500 ml 4-necked flask fitted with a mechanical stirrer, thermometer and condenser, under nitrogen, the compound of formula (II) obtained as described in Example 1 (3 g; 0.011 mol) is suspended at room temperature in a mixture of toluene (25 ml) and H$_2$O (25 ml). 30% NaOH (2.2 ml, 0.022 mol) is added, and the phases are separated. The aqueous phase is extracted with toluene (25 ml) and the combined organic phases are concentrated at low pressure. Bromoethanol (27.2 ml, 0.384 mol) and K$_2$CO$_3$ (7.9 g, 0.0572 mol) are then added to the residue thus obtained, and the mixture is heated at 70° C. for 16 hours. The mixture is then cooled to room temperature, diluted with toluene (2×30 ml) and treated with water (30 ml). The phases are separated and the organic phase is washed with a saturated solution of NaHCO$_3$ (30 ml) and a saturated solution of NaCl (30 ml), then dried on Na$_2$SO$_4$, and the solvent is eliminated at low pressure. The residue is taken up with AcOEt (30 ml) and treated with 37% HCl to pH=1. The resulting suspension is maintained under stirring for 12 hours, then filtered, and the solid obtained is washed with AcOEt (5 ml) and stove-dried at 50° C. under vacuum. 2 g of (bis-2-hydroxyethyl)-(2,4-dimethylphenylsulphanyl)-aniline hydrochloride of formula (VIII) is obtained with a yield of 50%.

$^1$H-NMR (300 MHz, DMSO-d6) δ: 7.38 (1H, d, J=7.8 Hz), 7.29 (1H, d, J=7.5 Hz) 7.22 (1H, s), 7.17-7.07 (2H, m) 6.74 (1H, t, J=7.8 Hz) 6.47 (1H, d, J=7.5 Hz) 3.46 (4H, t, J=6.6 Hz), 3.24 (4H, t, J=6.6 Hz) 2.32 (3H, s), 2.22 (3H, s).

EXAMPLE 4

Synthesis of (bis-2-methanesulphonyloxyethyl)-(2,4-dimethylphenylsulphanyl)aniline of Formula (IV)

In a 50 ml 3-necked flask fitted with magnetic stirring, thermometer and condenser, under nitrogen, the compound of formula (VIII) obtained as in Example 3 (1.7 g, 4.78 mmol) is suspended in toluene (10 ml), and the suspension is basified with triethylamine (2.68 ml, 0.019 mol). The mixture is cooled to 0° C. and treated by slow dripping with mesyl chloride (0.75 ml, 9.69 mmol), maintaining the temperature between 0 and 10° C. during the addition. At the end of the addition the reaction mixture is left to stand at a temperature of about 22° C., and when the reaction is complete, the mixture is washed with water (20 ml), the phases are separated, and the organic phase is concentrated at low pressure. The resulting (bis-2-methanesulphonyloxyethyl)-(2,4-dimethylphenylsulphanyl)-aniline of formula (IV) (2.15 g) is not further purified, and is used in a subsequent reaction.

$^1$H-NMR (300 MHz, CDCl$_3$) δ: 7.35 (1H, d, J=7.8 Hz), 7.28-7.03 (3H, m) 7.22 (1H, s), 6.94 (1H, dt, J=7.8 J=0.9 Hz) 6.51 (1H, dd, J=7.8 J=1.2 Hz) 4.30 (4H, t, J=5.7 Hz), 3.57 (4H, t, J=5.7 Hz) 3.00 (3H, s) 2.36 (3H, s), 2.29 (3H, s).

EXAMPLE 5

Synthesis of Vortioxetine of Formula (I)

The compound of formula (IV) obtained as in Example 4 (2 g; 4.23 mmol) is dissolved in a solution of NH$_3$ in 18.3% MeOH (10 ml), and the resulting solution is heated to 40° C. The starting solution is completely converted after 4 hours at 40° C. The end-of-reaction mixture is then concentrated to residue, and the residue obtained is diluted in AcOEt. The solution is washed with H$_2$O (10 ml) and concentrated to give 1.38 g of vortioxetine free base.

$^1$H-NMR (300 MHz, CDCl$_3$) δ: 7.35 (1H, d, J=7.8 Hz), 7.14 (1H, s) 7.08-7.00 (3H, m), 6.91-6.86 (1H, m) 6.53 (1H, d, J=8.4 Hz) 3.24-3.23 (8H, m), 2.35 (3H, s), 2.31 (3H, s).

EXAMPLE 6

Synthesis of 1-Benzyl-4-[2-(2,4-dimethylphenylsulfanyl)phenyl]piperazine of Formula (III)

In a 1000 ml three-necked flask, equipped with a mechanical stirrer, thermometer and reflux condenser the compound of formula (VIII), obtained as described in Example 3, (113.8 g, 0.306 mol) is suspended in toluene (500 ml) and water (200 ml). NaOH 30% (44.9, 0.337 mol) is added dropwise and the mixture is stirred at 25° C. The organic phase is separated and the solvent is removed under reduced pressure. The residue is dissolved in toluene (500 ml) and triethylamine (66.6 g, 0.658 mol) is added dropwise. The solution is cooled to 0-5° C. and methanesulfonyl chloride (74.2 g, 0.643 mol) is dropwise added keeping the temperature between 0 and 5° C. The reacting mixture is stirred at the same temperature for 45 minutes and then water (300 ml) is added keeping the temperature below 10° C. The mixture is heated up to 25° C. and the phases are separated. Benzylamine (104.9 g, 0.979 mol) is added to the organic phase and the reacting mixture is heated up to 30° C. for 12 hours. Water (300 ml) is added and the organic phase is separated, washed with water (300 ml) and the solvent is removed under reduced pressure. The crude residue is suspended in methanol (300 ml) and heated up to 45-50° C. The solution is cooled to room temperature and the suspension thus obtained is filtered, washed with methanol (100 ml) and dried under vacuum. 1-Benzyl-4-[2-(2,4-dimethylphenylsulfanyl)phenyl] piperazine of formula (III) is obtained (86.6 g) in 77% yield.

HPLC assay 98%.

$^1$H-NMR (300 MHz, CDCl$_3$) δ: 7.41-7.26 (5H, m), 7.16 (1H, s), 7.09-7.02 (3H, m), 6.88-7.82 (1H, m), 6.53 (1H, d, J=8.4 Hz), 3.62 (2H, s), 3.13 (4H, t, J=3.9 Hz), 2.69 (3H, m), 2.37 (3H, s), 2.33 (3H, s)

EXAMPLE 7

Synthesis of Crude Vortioxetine of Formula (I)

Ethyl chloroformate (39.9 g, 0.367 mol) is dissolved in toluene (60 ml) and the solution is heated to 50-55° C. A solution of compound of formula (III) (95.15 g, 0.245 mol), obtained as described in Example 6, in toluene (416 ml) is added dropwise and the reacting mixture is stirred at 50-55° C. for 4 hours and then at 25° C. for 12 hours. The mixture is again heated up to 50-55° C. and NaOH 30% (49 g, 1.31 mol) and water (190 ml) are added. The organic phase is separated and the solvent is removed under reduce pressure. The crude residue is dissolved in butanol (476 ml) and KOH (68.7 g, 1.23 mol) is added in one portion. The reacting mixture is heated to 110° C. for 2.5 hours and then cooled to 60° C. Water (380 ml) is added and the organic phase is separated and the solvent removed under reduced pressure. The residue is dissolved in toluene (200 ml) and the solvent is removed giving 111.51 g of crude vortioxetine of formula (I).

EXAMPLE 8

Synthesis of Vortioxetine Hydrobromide of Formula (I)

Crude vortioxetine of formula (I) (265 g), obtained as described in Example 7 starting from 0.593 mol of compound of formula (III) is suspended in toluene (1600 ml) and water (930). The suspension is heated to 80° C. and HBr 48% (101.1 g, 0.6 mol) is added dropwise. The suspension is left under stirring at 80° C. until complete dissolution. The aqueous phase is separated and the organic phase is extracted with water (2×940 ml). To the collected aqueous phases toluene (1400 ml) and NaOH 30% (126 g, 0.945 mol) are added and the mixture is left under stirring at 80° C. until complete dissolution. The organic phase is separated, cooled to 25° C. and treated with water (358 ml) and HBr 48% (101.1 g, 0.6 mol), dropwise added, keeping the temperature between 20 and 25° C. The suspension thus obtained is left under stirring for 12 hours, filtered, washed with water (2×300 ml) and dried under vacuum. Vortioxetine hydrobromide of formula (I) in crystalline form is obtained in 90% yield over two steps, and with a chemical purity higher than 99.9% calculated by HPLC.

$^1$H-NMR (300 MHz, CDCl$_3$) δ: 7.33 (1H, d, J=7.8 Hz), 7.25 (1H, s), 7.16-7.12 (3H, m), 6.88 (1H, m), 6.43 (1H, d, J=8.1 Hz), 3.21 (8H, m), 2.32 (3H, s), 2.24 (3H, s).

The invention claimed is:

1. A process for preparing a compound of formula (III), or a salt thereof,

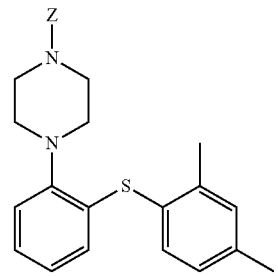

(III)

wherein Z is H or an amino protecting group, comprising reacting a compound of formula (IV), or a salt thereof,

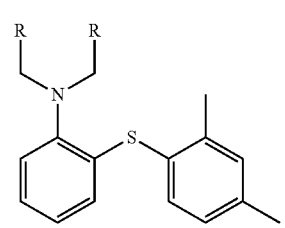

(IV)

wherein each of R substituents is an aldehyde group —CHO; or each of R substituents, being the same or different, is a carboxy group COOH or a reactive derivative thereof, or a —CH$_2$X group, wherein X is an halogen atom or a good leaving group, with a compound of formula (V), or a salt thereof,

NH$_2$—Z (V)

wherein Z is as defined above.

2. The process according to claim 1, wherein in a compound of formula (IV), or a salt thereof, both R substituents are the same.

3. The process according to claim 1, wherein the reaction of a compound of formula (IV), wherein each of R substituents is an aldehyde group —CHO, with a compound of formula (V) is performed under reductive amination conditions, in the presence of a reducing agent and a solvent.

4. The process according to claim 3, wherein the reducing agent is selected from NaCNBH$_3$, NaB(OAc)$_3$H, a homogenous or heterogeneous palladium (Pd) or platinum (Pt) metal based catalyst and molecular hydrogen, and a homogeneous or heterogeneous palladium (Pd) or platinum (Pt) metal based catalyst and a hydrogen donor under hydrogen transfer conditions.

5. The process according to claim 4, wherein NaB(OAc)$_3$H is generated in situ from NaBH$_4$ and acetic acid.

6. The process according to claim 1, wherein the reaction of a compound of formula (IV), wherein each of R substituents, being the same or different, is a —COOH group or a reactive derivative thereof, with a compound of formula (V) is performed under the amidation reaction conditions, with formation of an intermediate compound of formula (VI)

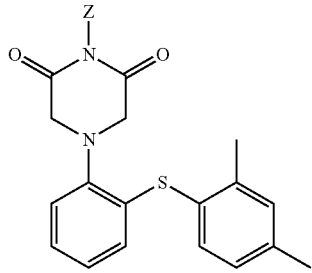
(VI)

wherein Z is as defined in claim 1, which is then converted into a compound of formula (III) by subsequent reduction with a hydride reducing agent, in a solvent.

7. The process according to claim 6, wherein the hydride reducing agent is selected from NaBH4 and LiAlH4.

8. The process according to claim 6 wherein the reduction reaction comprises the formation of an intermediate of formula (VII), or a salt thereof,

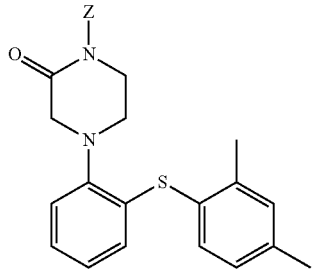
(VII)

wherein Z is as defined in claim 1.

9. The process according to claim 1, wherein the reaction of a compound of formula (IV), wherein each of R, being the same or different, is a —CH2X group with a compound of formula (V) is performed under the reaction conditions of the alkylating reactions, and, if the case, in the presence of a base and a solvent.

10. The process according to claim 9, wherein in a compound of formula (V) Z is H or benzyl.

11. The process according to claim 9, wherein in a compound of formula (V) Z is H, that is ammonia, and an excess of a compound of formula (V) is used with no need for an additional base.

12. The process according to claim 9, wherein the alkylation reaction is performed at a temperature ranging between about 0° C. and the solvent reflux temperature.

13. The process according to claim 9, wherein the alkylation reaction is performed at a temperature ranging about 10° C. and about 60° C.

14. The process according to claim 1, comprising the use as intermediate of a compound of formula (VI), (VII) or (VIII) or a salt thereof,

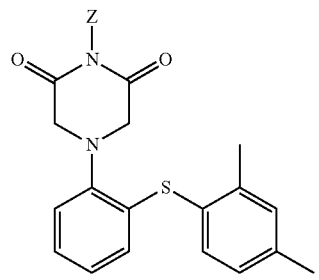
(VI)

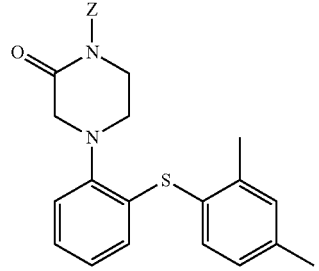
(VII)

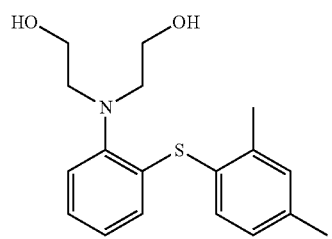
(VIII)

wherein Z is H or an amino protecting group.

15. Process for preparing vortioxetine of formula (I), or a salt thereof,

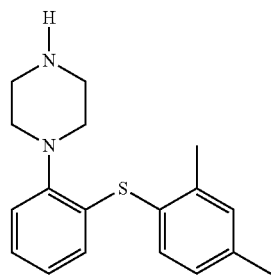
(I)

comprising reacting a compound of formula (IV) or a salt thereof,

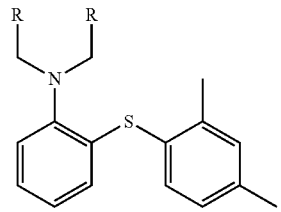
(IV)

wherein each of R substituents is an aldehyde group —CHO; or each of R substituents, being the same or different, is a carboxy group COOH or a reactive derivative thereof, or a —CH₂X group, wherein X is an halogen atom or a good leaving group,
with a compound of formula (V)

NH₂—Z (V)

wherein Z is H.

16. A compound selected from a compound of formula (IV), (VI), or (VII), or a salt thereof,

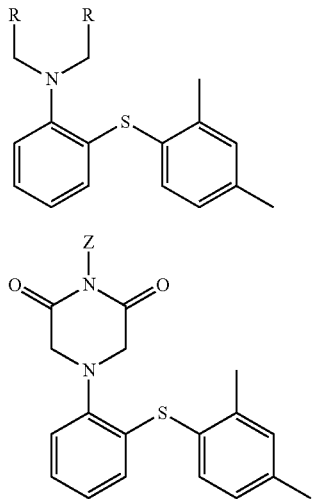

(IV)

(VI)

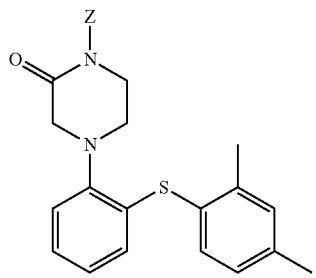

(VII)

wherein Z is H or an amino protecting group; and each of R substituents, being the same or different, is a carboxy group COOH or a reactive derivative thereof, or a —CH₂X group, wherein X is an halogen atom or a good leaving group, provided that when the R substituents are the same, they are other than —COOC₂H₅.

17. The process according to claim 15, wherein the resulting Vortioxetine of formula (I), or a salt thereof, has a chemical purity equal to or greater than 99.5%, calculated by HPLC.

18. The method of claim 1, further comprising, converting a compound of formula (III) into a salt thereof, and/or converting a salt of a compound of formula (III) into its free base.

19. The process according to claim 17, wherein the resulting vortioxetine of formula (I), or a salt thereof, has a chemical purity equal to or greater than 99.9%, calculated by HPLC.

* * * * *